United States Patent [19]

Lougheed et al.

[11] Patent Number: 5,233,404
[45] Date of Patent: Aug. 3, 1993

[54] OPTICAL SCANNING AND RECORDING APPARATUS FOR FINGERPRINTS

[75] Inventors: James H. Lougheed, Kinburn; Lam K. Chau, Gloucester, both of Canada

[73] Assignee: Oscan Electro Optics Inc., Gloucester, Canada

[21] Appl. No.: 589,813

[22] Filed: Sep. 26, 1990

[30] Foreign Application Priority Data

Sep. 29, 1989 [CA] Canada .................. 614358

[51] Int. Cl.⁵ .................................. B06K 9/74
[52] U.S. Cl. .................................. 356/71; 382/4; 250/227.19
[58] Field of Search .................. 356/71; 354/62; 250/227.19; 382/4

[56] References Cited

U.S. PATENT DOCUMENTS

| | | | |
|---|---|---|---|
| 3,200,701 | 8/1965 | White | 356/71 |
| 3,482,498 | 12/1969 | Becker | 356/71 |
| 3,527,535 | 9/1970 | Monroe | 356/71 |
| 3,968,476 | 7/1976 | McMahon | 340/146.3 |
| 4,210,899 | 7/1980 | Swonger et al. | 340/146.3 |
| 4,414,684 | 11/1983 | Blonder | 382/4 |
| 4,544,267 | 10/1985 | Schiller | 356/71 |
| 4,681,435 | 7/1987 | Kubota et al. | 356/71 |
| 4,792,226 | 12/1988 | Fishbine | 356/71 |
| 4,924,085 | 5/1990 | Kato et al. | 356/71 |

OTHER PUBLICATIONS

I.B.M. Technical Disclosure Bulletin, vol. 16, No. 11, Apr. 1974, p. 3572.

*Primary Examiner*—Vincent P. McGraw
*Assistant Examiner*—LaCharles Keesee
*Attorney, Agent, or Firm*—Dressler, Goldsmith, Shore, Sutker & Milnamow, Ltd.

[57] ABSTRACT

In an optical fingerprinting system a truncated prism is used. The prism has an imaging surface against which a finger is applied, an illumination surface substantially parallel to the imaging surface and an inclined viewing surface between the imaging and illumination surfaces. Opposite the included viewing surface is another inclined surface that is coated with light absorbent material. The remaining two end surfaces of the prism may also be similarly coated. When a light source is positioned beside the illumination surface light enters the prism and causes an image of the fingerprint to be invisible on the viewing surface. As a finger is rolled on the imaging surface a linear charge coupled device (CCD) may be moved in synchronism to record the whole image.

9 Claims, 2 Drawing Sheets

FINGERPRINT APPLICATION DIAGRAM

OPTICAL SCANNING AND RECORDING APPARATUS FOR FINGERPRINTS

BACKGROUND OF THE INVENTION

This invention related to an improved mechanism for obtaining human fingerprints without the use of ink by means of optical scanning.

It is known to provide an optical scanning mechanism utilizing a prism against which the finger is placed. By using the principle of Total Internal Reflection it is possible to obtain a view through such a prism of the areas of contact of the ridges of the human fingerprint with the surface of the prism, due to the frustration of the mechanism of Total Internal Reflection at those points where the skin ridges make contact with the surface. When so viewed, there is a difference in contrast between the points of contact of the fingerprint and the surrounding area. See for example, U.S. Pat. No. 3,482,498 (Becker), U.S. Pat. No. 4,414,684 (Blonder), U.S. Pat. No. 3,200,701 (White), U.S. Pat. No. 3,968,476 (McMahon), U.S. Pat. No. 4,210,899 (Swonger).

U.S. Pat. No. 3,527,535 (Monroe) illustrates the principle of using a dark field background to enhance the contrast of such fingerprints obtained using frustrated Total Internal Reflection. Monroe utilizes a dark opaque background in order to produce a light on dark image, significantly improving the contrast ratio available in the image. However, illumination is provided through the sides of the prism only, reducing the amount of light available through scattering from the points of contact of the skin ridges with the surface of the prism.

SUMMARY OF THE INVENTION

It is a principal object of the present invention to provide a fingerprint scanning mechanism of the general type disclosed by Monroe but which provides enhanced contrast ratio of the image and improved image capture and processing capabilities.

It is another object to provide, according to a specific embodiment of the invention consistent brightness throughout the finger contact area and additionally to provide low-cost high resolution image capturing using mechanical scanning in a tilted focal plane.

Thus, in one broad aspect of the invention, there is provided a prism means for use in a fingerprint imaging system comprising a body transparent to light having an imaging surface against which the finger to be imaged is placed, an illumination surface which is substantially parallel to the imaging surface and through which light from a source of illumination may enter the prism to strike the finger to be imaged at a substantially normal angle of incidence, a viewing surface located between the imaging surface and the illumination surface which lies at an acute angle with respect to the imaging surface, a further surface located between the imaging surface and the illumination surface and generally opposite the viewing surface such that the further surface is imaged on the viewing surface, the further surface being coated with a light absorbing coating to absorb light within the prism and prevent transmission of light into the prism from outside whereby, when a finger is placed on the imaging surface, a fingerprint image appears on the viewing surface, the fingerprint image consisting of bright fingerprint ridges on a dark background.

DETAILED DESCRIPTION OF PREFERRED EMBODIMENTS

Figure 1:
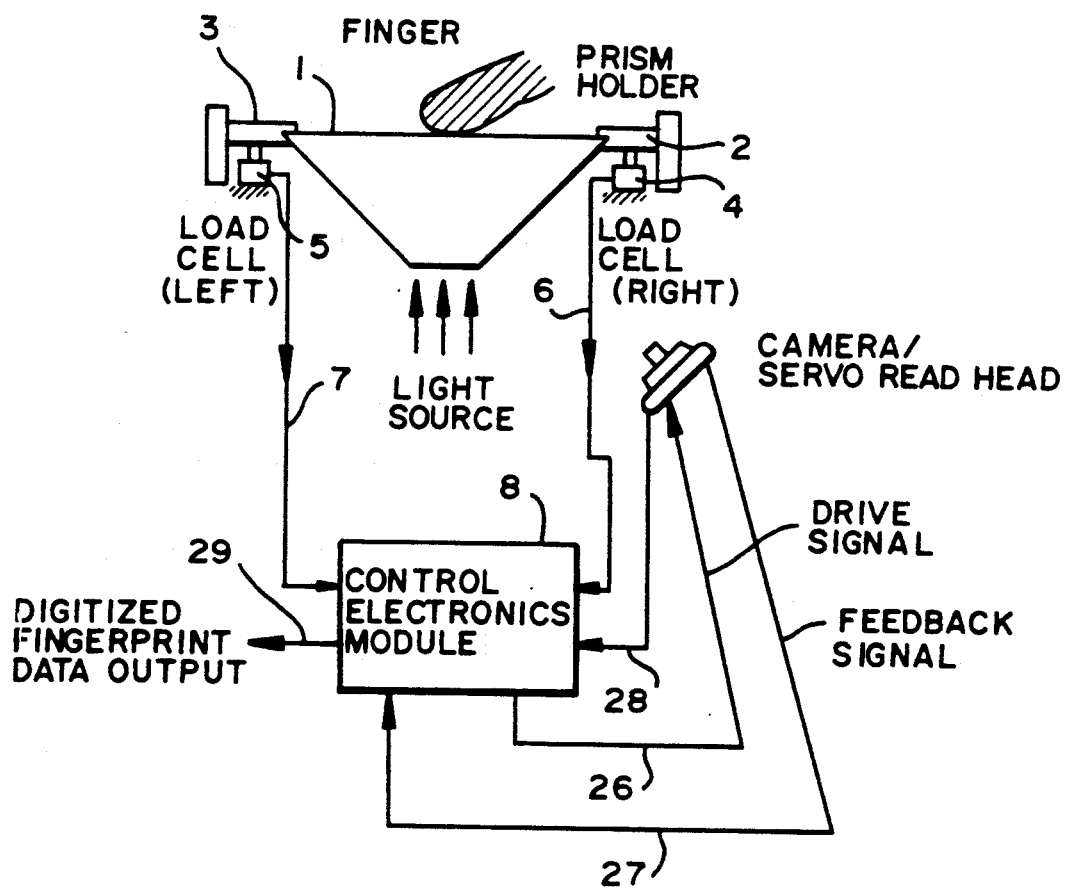
FIG. 1 is a schematic drawing of the system.

Referring to FIG. 1, a truncated prism 1 is provided, against the top surface of which the fingerprint to be imaged is applied. Prism holders 2, 3 maintain the truncated prism in place. Load cells 4, 5 attached to prism holders 2 and 3 are sensitive to the downward force placed upon them and output signal 6 and 7 respectively which are proportional to the magnitude of the force upon the respective load cells. By utilizing a balance beam effect, it is possible for the control electronics module 8 to determine the lateral position of the finger as shown in FIG. 1 at any given time relative to the load cells. This information is then used to control the positioning of a portion of a so-called camera 9 as will be explained in detail hereinafter.

Figure 2:
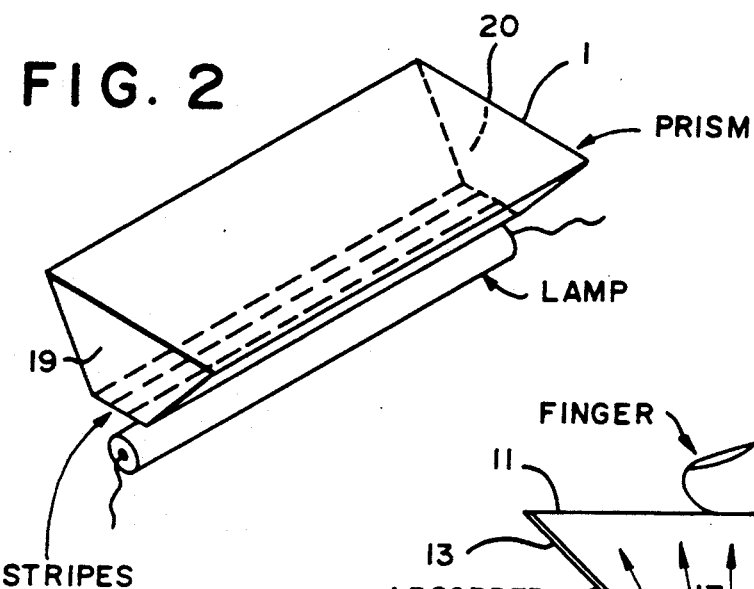
FIG. 2 is a perspective view of one embodiment of the prism arrangement for use in the invention.
Figure 3:
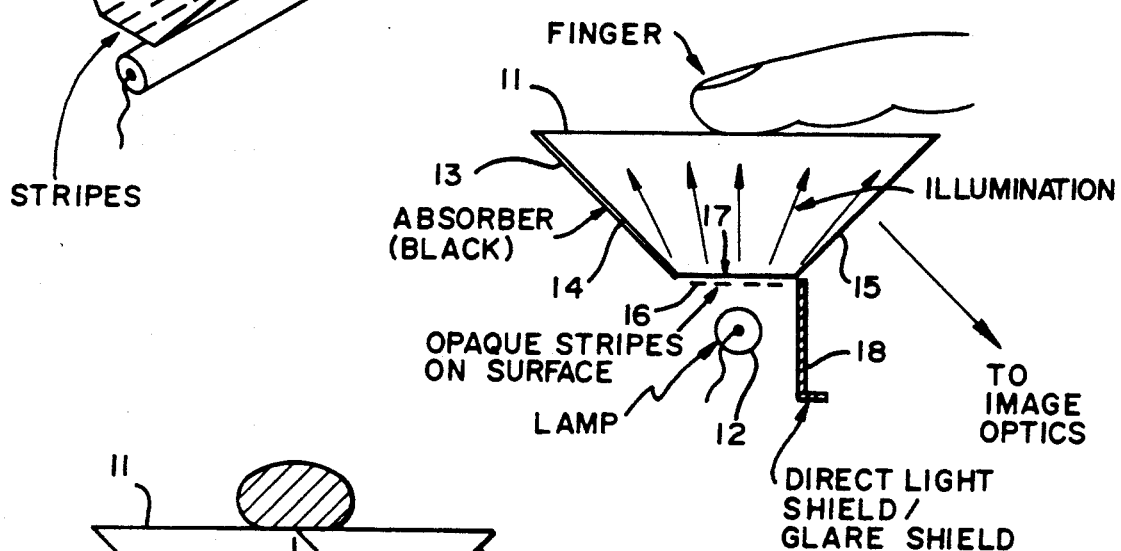
FIG. 3 is a side elevation view of other details of the prism arrangement.

FIG. 2 and FIG. 3 illustrate the general arrangement of the prism 1. The prism is made of any suitable material transparent to light and having a refractive index greater than that of air. Both glass and plastics are suitable types of materials for the manufacture of the prism.

The prism of the preferred embodiment is manufactured in the shape of a truncated prism, that is to say with its apex removed and a flat surface disposed in its place parallel to the opposite side of the prism. A light source 12 is shone through the truncated apex directly onto the opposite surface 11 of the prism at a substantially normal angle of incidence. This surface 11 form an interface between the material of the prism and the surrounding air such that light striking the interface at angles greater than the critical angle, measured normally to the interface, is totally reflected internally. Light striking the surface at angles below the critical angle, measured normally to the interface, is refracted and passes through. The critical angle for glass or plastics is typically of the order of 42°. Therefore, light striking the interface from the light source 12 disposed below the truncated apex of the prism will generally strike the interface 11 and pass through into the surrounding air.

On the rear face 13 of the prism and on parallel end surfaces 19, a light absorbing coating 14 is applied in order to prevent light from passing through the surface from outside or being reflected internally. Consequently, little or no light will emanate from surface 13 in such a fashion that it will be reflected internally by surface 11 and visible through surface 15. Consequently, the view through surface 15 into the prism will be dark as all illumination from lamp 12 will pass through the prism surface 11 and out into the air above the prism. It is noted that, although light absorbing coatings are preferred on the parallel end surfaces 19 and 20 to reduce reflections, these are not absolutely necessary.

When a finger is applied to the top or imaging surface 11, the ridges of the fingerprint which makes direct contact with the prism will cause light to be dispersed back into the prism and some of this light will pass through viewing surface 15 whereas the valleys of the fingerprint which do not come into contact with the prism will continue to appear dark when viewed through the prism at or above the critical angle. Accordingly, when viewed through surface 15 above the critical angle, a sharply delineated fingerprint image will be visible against a dark background.

Stripes 16 of opaque material may be provided along the illumination surface 17 of the prism such that there is more opaque material in the middle than at the ends (i.e. where surface 17 joints surfaces 13 and 15). This has the effect of equalizing the light intensity from source 12 to provide even illumination of the contact area of the finger with surface 11 and to substantially correct for illumination drop-off along the contact surface due to perspective. The provision of the stripes of opaque material ensures that illumination is substantially even along both axes of the area of contact of the finger with imaging surface 11. The same equalization effect could be achieved by other means, for example, by coating the lamp 12 itself is a gradiated thickness or density fashion to again reduce the illumination near the centre.

In addition, a light shield 18 is provided to prevent light from source 12 reaching the observer directly. In consequence, essentially all of the light reaching an observer viewing through viewing surface 15 above the critical angle will come from only the light scattered by the ridges of the fingerprint against contact surface 11, thus providing a fingerprint image with greatly enhanced contrast.

The prism may be in the form of a truncated triangle in profile as shown or any other shape having two sides which meet at an acute angle. In such a case, it is most preferable that one of the faces defining the acute angle meet two other faces which are parallel to each other, one of these serving as an imaging surface and the other as an illumination surface. However, even if the illumination surface is not parallel to the imaging surface, the principle of the invention could still be achieved but with less efficiency. Even if the apex were left intact and the light directed through the apex itself, the principle of the invention could be demonstrated although the very uneven illumination of the imaging surface would cause uneven brightness of the image.

Figure 4:
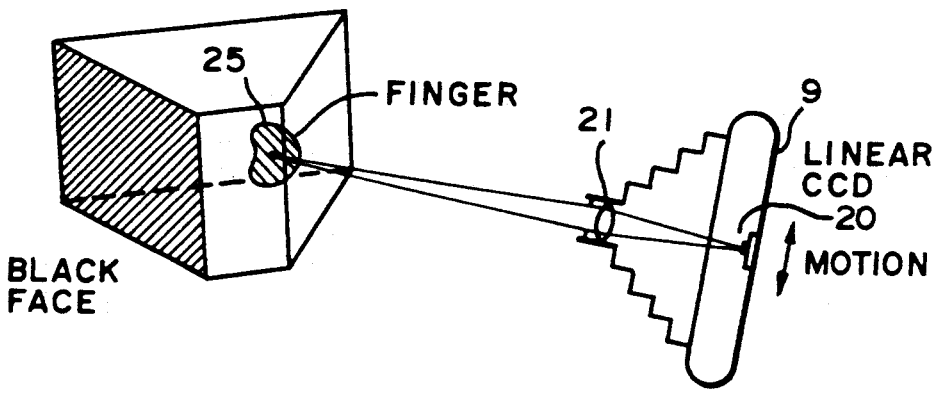
FIG. 4 is a perspective view of the relationship between the prism and CCD camera.

FIG. 1 and FIG. 4 show the means by which image data is captured. As the finger is rolled on the prism in order to produce a rolled fingerprint as is customary, load cells 4 and 5 sense the relative position of the finger on the prism and produce output signals 6 and 7 which are fed to the control electronics module 8. This module is then used to move linearly a linearly arranged CCD (charge coupled device) sensor 20 incorporated in camera 9 and shown in FIG. 4. Light from the contact surface 11 is focused by an optical lens 21 onto the CCD sensor 20. As the CCD sensor is essentially linear, the fingerprint information focused on the CCD sensor will represent a linear sampling across one direction of the fingerprint image on viewing surface 15. The CCD sensor is only capable of reading a line of information at a time, thus necessitating the CCD 20 to be scanned across the width of the fingerprint image 25 shown in FIG. 4. The control electronics module 8 in FIG. 1 provides a signal on a drive line 26 to move CCD 20 in accordance with the positioning of the finger on the prism 1 at any given time in order to produce an optimized set of data readings to the CCD sensor representing a full rolled fingerprint image. As shown in FIG. 1, a feedback line 27 from camera 9 to module 8 for positioning of the CCD 20 is provided as well as an analog line 28 which feeds analog signals from the CCD 20 to the module 8. Module 8 processes these analog signals to provide a digitizing fingerprint data output on line 29.

For example, it is possible to perform manipulations to the data to invert the contrast such that light areas are displayed as dark and dark areas displayed as light. In this case, the ridges would then be dark and the valleys and background light, rendering an image equivalent to an ink impression, through retaining the contrast advantage obtained by means of the dark field illumination used to obtain the image in the first place.

Similarly, computer processing will allow scaling of the image to any desired size and the juxtapositioning of multiple images in order to obtain composite images. An example of such a composite image would be all of the fingers on a hand for instance. These as well could then be scaled, inverted if desired and otherwise manipulated to be printed and displayed in an optimum fashion.

Although not shown in the drawings, it is also possible to obtain an image of contact of a fingerprint over more than a single plane. The use of a partially compliant prism surface 11 would permit more of the fingerprint pattern to be visible at any given time. This would allow side features of the finger to be obtained without rolling and would also allow patterns from rounded parts of the body such as the palm to be imaged in a better fashion.

Such a compliant prism would be fluid filled with the contact surface made of thin plastic. A constantly descending index of refraction from the contact surface through the prism would need to be maintained with the contact surface being somewhat stiffer than the skin of the human finger so that air gaps were maintained between the prism surface and the valleys.

Figure 5:
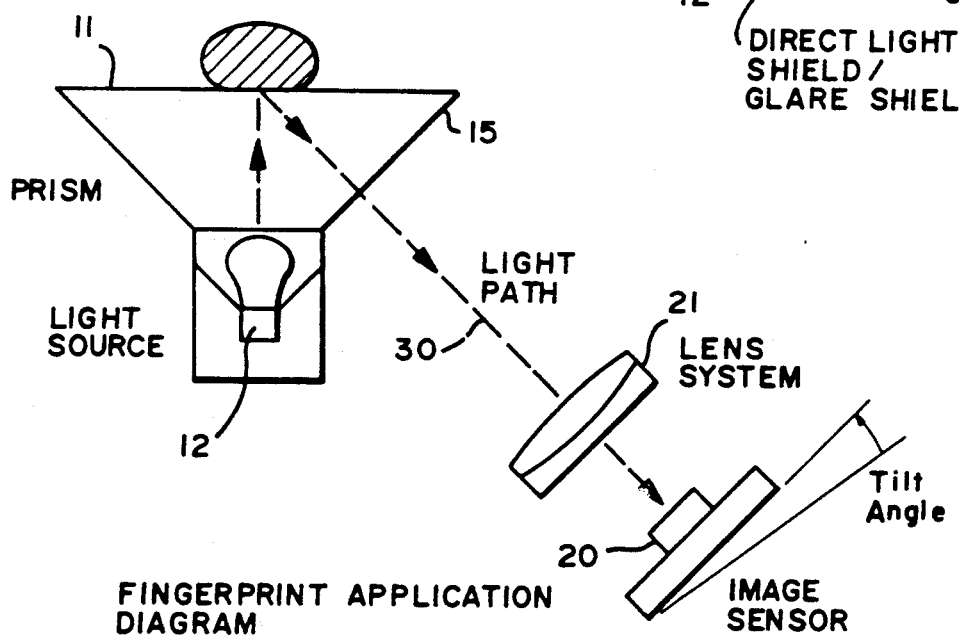
FIG. 5 is a schematic view illustrating a refinement of the system.

It should be noted that because the finger is rolled along imaging surface 11 and viewed through viewing surface 15 which is inclined at an angle to surface 11 some defocusing caused by differences in depth of view occurs. This can be compensated for, as shown in FIG. 5, by tilting the linear CCD 20 out of normal with regard to the optical axis 30 through lens 21. The tilt angle will depend on different parameters such as the refractive index of the prism material and the prism angles but typically a tilt angle of between 30° and 35° has proven advantageous.

As described above, the CCD 20 alone, rather than the whole camera is moved as the finger is rolled. In general the inertia of the camera and lens assembly would be too great to use movement of the assembly for scanning during rolling of a finger. However, where a plain impression of four stationary fingers is to be obtained the inertia of the camera is not problematic and so the whole camera can be moved to capture the image of all four prints.

Although a CCD is particularly described, any suitable photosensitive detector means such as a charge injection device (CID) or photodiode array could be used.

Additional modifications are proposed below.

In FIG. 5, the tilting of the linear CCD array axis will compensate for the defocusing effect, but will not correct the keystone distortion due to different magnifications of points along the projected image along the CCD element. The result is compression of pixels at one end, and expansion at the other. A proposed method which has been tested by prototypes to linearize the image pixels if the following: First all pixels on the linear CCD array are partitioned into groups according to the degree of compression or expansion as calculated from simple geometric optics. For example a 2000-element CCD may be partitioned into 200 groups each of which has more or less piecewise-linear elements within. The number of elements per group is such chosen that the representative pixel of each group, after some signal processing such as an averaging operation in its simplest form, forms the element of a uniform image of reduced element size. In other words, this method maps 2000 non-uniform pixels into 200 uniform pixels in the image plane through geometric calculations, element partitioning, and image processing. This is essentially a tradeoff between resolution and non-uniformity of the image pixels.

A rolled impression of a finger can also be made by manually rolling the finger at a speed guided by two moving illuminated lines. The speed of movement of the two illuminated lines is in synchronism with the scanning speed of the CCD 20 of FIG. 4.

Fingerprint recognition can be applied using the scanning mechanism described in this application. A proposed method which has been demonstrated by a prototype successfully involves pixel-by-pixel cross correlation estimation between a template and a freshly obtained fingerprint from a live finger. This is essentially done by hardware: A person first makes a template of his single digit such as a thumb. During a recognition process, the same digit is scanned and stored in a larger bit map. A search window is then moved around to approximately the centre of the fingerprint where there is most ridge information. Within this search window another window having the same size of the template is moved systematically from left to right, up and down to cover the entire area of search window. For each new coordinate position of this recognition window, hardware cross correlation is done between the template pattern and the recognition window pattern. A threshold is set to declare a match or no-match. In order to apply the right amount of pressure to make an optical print, a handle mechanism is used to steady the hand before a thumb print is made. A thumb print recognizer can be conveniently combined with a door lock with a handle and with which thumb pressure is used to unlatch the locking bolt.

It is important that the thumb be placed in the same position in the recognizer as the position by which the template was obtained. For that purpose, a guide for the thumb may be attached to the handle so that when the thumb is in the guide the correct thumb position for the recognizer is established. One such guide that is proposed is a generally U-shaped spring clip which can be mounted such that the sides of the U project upwardly from the imaging surface of the prism. Preferably the clip holds a thumb by the thumb joint bone at its largest cross section as shown. This ensures a reference fixed position to be established each time a template is taken and each time a live thumbprint is taken for access control or other biometrics applications.

We claim:

1. An apparatus for use in a fingerprint imaging system comprising:

a) a source of illumination, b) a prism comprising a body transparent to light having:

an imaging surface against which the finger to be imaged is placed, an apex opposite the imaging surface and located proximate the source of illumination such that light from the source of illumination may enter the prism through the apex to strike the finger to be imaged, a viewing surface located between the imaging surface and the apex which lies at an acute angle with respect to the imaging surface, a further surface located between the imaging surface and the apex and generally opposite the viewing surface such that the further surface is imaged on the viewing surface, the further surface being coated with a light absorbing coating to absorb light within the prism and prevent transmission of light into the prism from outside;

c) imaging means for capturing a fingerprint image arranged on an optical path which exits the viewing surface, the optical path within the prism intersecting the imaging surface at the location of the finger to be imaged at an angle greater than the critical angle; and d) a light shield means to prevent light from the source of illumination being transmitted directly to the imaging means;

whereby, when a finger is placed on the imaging surface, a fingerprint image appears on the viewing surface on the optical path, the fingerprint image consisting of bright fingerprint ridges on a dark background.

2. The apparatus defined in claim 1 in which all surfaces of the prism except the imaging surface, viewing surface and apex are coated with light absorbent material.

3. An apparatus for use in a fingerprint imaging system comprising:

a) a source of illumination;

b) a prism comprising a body transparent to light and being shaped in profile as a truncated triangle having:

a base serving as an imaging surface against which the finger to be imaged is placed, a truncated surface serving as an illumination surface which is substantially parallel to the imaging surface and located proximate the source of illumination such that light from a source of illumination may enter the prism through the illumination surface to strike the finger to be imaged at a substantially normal angle of incidence, the illumination surface having thereon opaque stripes serving to equalize substantially illumination across the imaging surface, a first inclined surface serving as a viewing surface located between the imaging surface and the illumination surface which lies at an acute angle with respect to the imaging surface, a second inclined surface located between the imaging surface and the illumination surface and generally opposite the viewing surface such that the second inclined surface is imaged on the viewing surface, the second inclined surface being coated with a light absorbing coating to absorb light within the prism and prevent transmission of light into the prism from outside, and two parallel end surfaces;

c) imaging means for capturing a fingerprint image arranged on an optical path which exits the viewing surface, the optical path within the prism intersecting the imaging surface at the location of the finger to be imaged at an angle greater than the critical angle; and d) a light shield means to prevent light from the source of illumination being transmitted directly to the imaging means;

whereby, when a finger is placed on the imaging surface, a fingerprint image appears on the viewing surface on the optical path, the fingerprint image consisting of bright fingerprint ridges on a dark background.

4. A fingerprint imaging systems comprising:

prism means;

illumination means;

load cell means at supports for the prism;

camera means including a linearly arranged photosensitive detector means; and servo means for positioning the photosensitive detector means in response to signals from the load cell means as a finger is rolled on the prism; and image processing and storage means; wherein the prism means comprises a body transparent to light having an imaging surface against which the finger to be imaged is placed;

an illumination surface which is substantially parallel to the imaging surface and through which light from a source of illumination may enter the prism to strike the finger to be imaged at a substantially normal angle of incidence, a viewing surface located between the imaging surface and the illumination surface which lies at an acute angle with respect to the imaging surface and through which the fingerprint image is transmitted to the photosensitive detection means, a further surface located between the imaging surface and the illumination surface and generally opposite the viewing surface such that the further surface is imaged on the viewing surface, the further surface being coated with a light absorbing coating to absorb light within the prism and prevent transmission of light into the prism from outside, the photosensitive detector means being arranged on an optical path which exits the viewing surface, the optical path within the prism intersecting the imaging surface at the location of the finger to be imaged at an angle greater than the critical angle;

whereby, when a finger is placed on the imaging surface, a fingerprint image appears on the viewing surface on the optical path, the fingerprint image consisting of bright fingerprint ridges on a dark background.

5. The system defined in claim 4 wherein the shape of the prism in profile is that of a truncated triangle having a base serving as the imaging surface, a truncated surface serving as the illumination surface, a first inclined surface serving as the viewing surface, a second inclined surface which is the coated further surface and two parallel end surfaces.

6. The system defined in claim 5 wherein means are provided to equalize substantially illumination across the imaging surface.

7. The system defined in claim 6 wherein the equalization means is opaque stripes provided on the illumination surface.

8. The system defined in claim 4 wherein the photosensitive detector means is a CCD.

9. The system defined in claim 4 wherein the photosensitive detector means is tilted at an angle with respect to the light path from the imaging surface to compensate for depth of view differences.

* * * * *